United States Patent
Aikawa et al.

(10) Patent No.: US 7,101,532 B2
(45) Date of Patent: *Sep. 5, 2006

(54) LIPOSOME CONTAINING HYDROPHOBIC IODINE COMPOUND

(75) Inventors: Kazuhiro Aikawa, Kanagawa (JP); Hiroshi Kitaguchi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 392 days.

This patent is subject to a terminal disclaimer.

(21) Appl. No.: 10/258,801

(22) PCT Filed: Apr. 26, 2001

(86) PCT No.: PCT/JP01/03629

§ 371 (c)(1),
(2), (4) Date: May 15, 2003

(87) PCT Pub. No.: WO01/82977

PCT Pub. Date: Nov. 8, 2001

(65) Prior Publication Data

US 2003/0180220 A1    Sep. 25, 2003

(30) Foreign Application Priority Data

Apr. 28, 2000  (JP) ............................ 2000-130069
Jan. 26, 2001  (JP) ............................ 2001-018573

(51) Int. Cl.
*A61K 49/04* (2006.01)

(52) U.S. Cl. .................... 424/9.4; 424/1.11; 424/1.45; 424/1.65; 424/450

(58) Field of Classification Search ................ 424/9.4, 424/9.44, 9.454, 9.455, 450, 1.11, 1.65, 1.45, 424/489; 552/544; 436/71

See application file for complete search history.

(56) References Cited

U.S. PATENT DOCUMENTS 4,192,859 A     3/1980 Mackaness et al.
5,550,263 A *  8/1996 Herslof et al. ............... 554/78

FOREIGN PATENT DOCUMENTS

GB    2157283 A * 10/1985

OTHER PUBLICATIONS

XP-002301540—R. H. Seevers et al., "Potential Turmor- or Organ-Imaging Agents. 23. Sterol Esters of Iopanoic Acid", J. Med Chem. (1982), vol. 25., No. 12, pp. 1500-1503.
XP-002302389—Werner Krause, "Delivery of diagnostic agents in computed tomography" Elsevier Science B. V. (1999), pp. 159-173.
Supplementary European Search Report dated Nov. 5, 2004.

* cited by examiner

*Primary Examiner*—Dameron L. Jones
(74) *Attorney, Agent, or Firm*—Sughrue Mion, PLLC

(57) ABSTRACT

A liposome containing a hydrophobic iodine compound such as a 1,3,5-triiodobenzene derivative having at least one substituent containing 18 or more carbon atoms as a membrane component, and an X-ray contrast medium containing the liposome for use in radiography of a vascular disease and the like.

6 Claims, 8 Drawing Sheets

Fig. 1

Proliferation curve of vascular smooth muscle cells

Days after inoculation

Fig. 2

Number of vascular smooth muscle cells

Days after inoculation

Fig. 3

Proliferation curve of rat vascular smooth muscle cells

Fig. 4

Proliferation curve of rabbit smooth muscle cells

Before administration

Fig. 9 (B)

Immediately after administration

Fig. 10 (A)

15 minutes after administration

Fig. 10 (B)

30 minutes after administration

LIPOSOME CONTAINING HYDROPHOBIC IODINE COMPOUND

TECHNICAL FIELD

The present invention relates to a liposome. More specifically, the invention relates to a liposome that can be utilized for a method for selectively accumulating a hydrophobic iodine compound in a pathological lesion and imaging said lesion in contrast to non-pathological site.

BACKGROUND ART

In the modern society, especially in the societies of advanced countries, opportunities of ingesting high calorie and high fat diet are increasing. For this reason, mortalities due to ischemic diseases resulting from arteriosclerosis (heart diseases such as myocardial infarction and angina pectoris, cerebrovascular diseases such as cerebral infarction and cerebral hemorrhage) have been increasing. Therefore, it has been desired to diagnose such conditions at an early stage to employ an appropriate treatment. However, no satisfactory method is available for diagnosing progress of arteriosclerosis at an early stage before the onsets of the aforementioned diseases.

Methods for diagnosing arteriosclerosis are basically classified into non-invasive methods and invasive methods in which a catheter or the like is inserted into an artery. Among them, typical non-invasive methods include X-ray angiography and ultrasonography. However, by these methods, it is almost impossible to detect arteriosclerosis at an early stage, especially constriction of coronary artery, which causes myocardial infarction or angina pectoris, at an early stage before the onset of these diseases.

CT, MRI and the like may sometimes be used as another class of non-invasive methods. However, these methods have been mainly developed for detection of tumors, and accordingly, they have a problem of a low resolution of arteriosclerotic lesions. In addition, the methods require expensive and large-scale apparatuses, which limits employable hospitals and general applicability. Further, methods utilizing radioisotopes have also been investigated. However, these methods still remain at an experimental level.

As the invasive methods, intravascular echo, vascular endoscope and the like have been used. It is recognized that an arteriosclerotic lesion with a thickness as thin as 0.1 mm can be measured by these methods. However, for employment of these methods, it is necessary to arterially insert an ultrasonic oscillator or an endoscope attached to an end of a catheter, which may result in serious physical stress and heaviness as well as a risk of a patient. Therefore, although these methods have been used therapeutically for patients after the attack of myocardial infarction and the like or as secondary prophylaxis, they cannot be used for a diagnostic purpose to know as to presence or absence or a degree of progress of arteriosclerosis in a patient before onset.

Among the aforementioned methods, a method most widely used for identification of a lesion of arterial vasoconstriction is X-ray angiography. This method comprises the step of administration of a water-soluble iodine contrast medium to visualize vascular flows, and detecting a lesion at which the flows are obstructed. However, these methods can only detect a lesion where constriction progresses 50% or more and fail to detect a lesion before the onset of attack of an ischemic disease.

Separately from the above methods, attempts have also been reported in which a hydrophobic iodine contrast medium or a hydrophilic contrast medium is formulated for selective accumulation in a target lesion (International Patent Publications WO95/19186, WO95/21631, WO89/00812, British Patent No. 867650, WO96/00089, WO94/19025, WO96/40615, WO95/2295, WO98/41239, WO98/23297, WO99/02193, WO97/06132, U.S. Pat. Nos. 4,192,859, 4,567,034, 4,925,649, Pharm. Res., 16 (3), 420 (1999), J. Pharm. Sci., 72 (8), 898 (1983), Invest. Radiol., 18 (3), 275 (1983). For example, Pharm. Res., 16 (3), 420 (1999) discloses that, by injection of an oil-particle dispersion of cholesteryl iopanoate as a hydrophobic compound, the iodine compound accumulates in arteriosclerotic lesions of experimental animals.

Further, J. Pharm. Sci. 72 (8), 898 (1983) discloses examples of X-ray hepatography and splenography by injection of an oil-particle dispersion of cholesteryl iopanoate. U.S. Pat. No. 4,567,034 describes a method of selective hepatography or splenography utilizing liposomes encapsulating an ester of diatrizoic acid. International Patent Publications WO96/28414 and WO96/00089 disclose contrast media for imaging vascular pools or lymphatic systems. However, the methods using these formulations are not satisfactory in efficiency and selectivity for a purpose of selective contrast of vascular diseases, and no example thereof is reported in which vascular diseases are imaged by utilizing X-ray irradiation.

Mechanisms of onset of arterial diseases have recently been progressively elucidated at levels of genes, proteins and cells (*J. Biol. Chem.*, 1996, 271 (44) 27346–52; Nature, 386 (6662) 292–6). As for arteriosclerosis, it has been elucidated that plural kinds of cells form lesions while they mutually control their proliferation (Arterioscler. Throm. Vasc. Biol., 1999 (3) 461–71; Lab Invest 1998, 78 (4) 423–34). However, no example has been demonstrated which reproduces the state of a lesion, in which plural kinds of cells are involved as mentioned above, in a cell culture vessel, and accordingly, evaluation of drugs for arteriosclerosis or restenosis have so far been conducted mainly by using model animals.

However, such methods using animals are time-consuming and require a high cost, and their use is also required to be minimum from a viewpoint of prevention of cruelty to animals. Therefore, an in vitro evaluation method of reproducing a state of arteriosclerotic lesion has been desired for screening of a large number of compounds for a short period of time.

DISCLOSURE OF THE INVENTION

An object of the present invention is to provide means for selectively accumulating an iodine compound in a lesion of a vascular disease caused by abnormal proliferation of vascular smooth muscle cells such as arteriosclerosis and restenosis after PTCA. Another object of the present invention is to provide a means for imaging of a biological environment of a vascular disease or the like by X-ray radiography using the aforementioned means. The inventors of the present invention conducted various studies to achieve the foregoing objects, and as a result, they found that liposomes containing a hydrophobic iodine compound as one of membrane components accumulated in vascular smooth muscle cells and foam macrophages, which are main components of arteriosclerotic lesion.

A further object of the present invention is to provide a cell culture system reproducing a state of lesion of arteriosclerosis, restenosis or the like and a method for producing such a cell culture system. Another object of the present invention is to provide a method for evaluating a drug for arterial diseases by using the aforementioned means. The inventors of the present invention conducted various studies to achieve the foregoing objects, and as a result, they found that a cell culture system reproducing a state of lesion of arteriosclerosis, restenosis or the like was successfully provided by simultaneously culturing in a single cell culture vessel two or more kinds of cell species that form a lesion of a mammalian disease. The present invention was achieved on the basis of these findings.

The present invention thus provides a liposome containing a hydrophobic iodine compound as a membrane component. As preferred embodiments of the present invention, provided are the aforementioned liposome, wherein the hydrophobic iodine compound is a 1,3,5-triiodobenzene derivative having at least one substituent containing 18 or more carbon atoms; the aforementioned liposome, which contains a lipid selected from the group consisting of phosphatidylcholines and phosphatidylserines as a membrane component; the aforementioned liposome, which contains a phosphoric acid dialkyl ester which is a diester of an alkyl containing 6 or more carbon atoms as a membrane component; and the aforementioned liposome, wherein the substituent containing 18 or more carbon atoms is a residue of a cholesterol derivative.

From another aspect, the present invention provides an X-ray contrast medium, which comprises the aforementioned liposome. As preferred embodiments of the invention, provided are the aforementioned X-ray contrast medium, which is used for radiography of a vascular disease, preferably radiography of vascular smooth muscle cells which are abnormally proliferated under an influence of foam macrophages, for example, for radiography of an arteriosclerotic lesion or restenosis after PTCA. The present invention also provides a method for contrasting a vascular disease, which comprises a step of X-ray radiography using the aforementioned liposome, and use of the aforementioned liposome for the manufacture of the aforementioned X-ray contrast medium.

From a further aspect, the present invention provides a method for preparing a cell culture system, which comprises a step of simultaneously culturing, in a single cell culture vessel, two or more kinds of cell species which are involved in formation of a lesion of a mammalian disease. As preferred embodiments of the invention, provided are the aforementioned method, wherein the cell species comprise primary culture cells isolated from a living body or established subculture cells; the aforementioned method, wherein the cell species comprise mammalian primary culture cells; and the aforementioned method, wherein the mammalian disease is a human disease.

As more preferred embodiments of the above invention, provided are the aforementioned method, wherein at least one of the cell species consists of cells involved in formation of arteriosclerotic lesion; the aforementioned method, wherein the cell species are selected from the group consisting of macrophages, vascular smooth muscle cells, and vascular endothelial cells; the aforementioned method, which comprises a step of culturing two kinds of cell species, in a single culture vessel, under being partitioned off by means of a cell filter; and the aforementioned method, wherein the two kinds of cell species consist of macrophages and vascular smooth muscle cells. As a particularly preferred embodiment of the present invention, provided is a method for producing a cell culture system that reproduces a state of an arteriosclerotic lesion, which comprises simultaneously culturing in a single culture vessel two kinds of mammalian primary culture cells involved in formation of arteriosclerotic lesion under being partitioned off by mean of a cell filter.

The present invention further provides a cell culture system, which is obtainable by the aforementioned method for producing a cell culture system. The present invention also provides a method for screening a drug by using a cell culture system that is obtainable by the aforementioned method for producing a cell culture system. As preferred embodiments, the present invention provides a method for determining effectiveness of a drug on a vascular disease, which comprises determining action of the drug on vascular smooth muscle cells proliferated by culturing foam macrophages and the vascular smooth muscle cells under being partitioned off by means of a cell filter; and a method for evaluating permeation ability of a drug into a lesion of vascular disease, which comprises measuring action of the drug on vascular smooth muscle cells proliferated by culturing foam macrophages and the vascular smooth muscle cells under being partitioned off by means of a cell filter.

BEST MODE FOR CARRYING OUT THE INVENTION

A type of the hydrophobic iodine compound is not particularly limited. For example, an iodobenzene derivative is preferred. More preferred is a 1,3,5-triiodobenzene derivative having at least one substituent having 18 or more carbon atoms. The substituent having 18 or more carbon atoms is preferably a hydrophobic group for stable localization of the 1,3,5-triiodobenzene residue, as being an iodine contrasting moiety, in a bilayer of the liposome. For example, preferred is a substituent having 20 or more carbon atoms in which the total number of oxygen atom and nitrogen atom is 10 or less. The hydrophobic substituent more preferably has a structure similar to that of lipid components constituting biological membranes. Preferred examples of a hydrophobic iodine compound that satisfies such conditions include, for example, 1,3,5-triiodobenzene derivatives having a cholesterol derivative residue as a substituent disclosed in J. Med. Chem., 25 (12), 1500 (1982); Steroids, 49 (6), 531 (1987); Pharm. Res., 6 (12), 1011 (1989); International Patent Publications WO95/19186, WO96/28414 and the like.

As the cholesterol derivatives, those described in the aforementioned publications are preferred, and cholesterol is particularly preferred. Preferred are compounds in which cholesterol is bound to a hydrophobic iodine compound, such as 1,3,5-triiodobenzene, via the 3-hydroxyl group. For binding of the hydroxyl group of cholesterol and the hydrophobic iodine compound such as 1,3,5-triiodobenzene, for example, means such as an ester bond, ether bond, urethane bond, and carbonic acid ester bond can be used. An ester bond is preferred. Cholesterol and the hydrophobic iodine compound such as 1,3,5-triiodobenzene may be directly bound via any of the aforementioned bonds, or bound via an appropriate bridging group. Examples of suitable bridging group include a linear or branched alkylene group having 5 or less carbon atoms.

The hydrophobic iodine compound, preferably 1,3,5-triiodobenzene compound, may have one or more substituents other than the aforementioned substituent having 18 or more carbon atoms. The type, substituting position and numbers of the substituents are not particularly limited. For example, it is preferred that a substituted or unsubstituted amino group, a substituted or unsubstituted acylamino group, a hydroxyl group, a carboxyl group or the like substitutes on the benzene ring of the hydrophobic iodine compound. Preferred substituents are a substituted or unsubstituted amino group and a substituted or unsubstituted acylamino group. Examples of the amino group having a substituent include a monoalkylamino group, a dialkylamino group and the like, and examples of the acylamino group having a substituent include trifluoroacetylamino group, p-chlorobenzoylamino group and the like.

Preferred examples of the hydrophobic iodine compound are listed below. However, the liposomes of the present invention are not limited to those containing these compounds.

Compound (1)

Compound (2)

Compound (3)

Compound (4)

-continued

Compound (5)

Compound (6)

Compound (7)

Compound (8)

Compound (9)

The hydrophobic iodine compound is contained as a component of a membrane of the liposome, and a content of the compound in the liposome is about from 10 to 90 mass %, preferably from 10 to 80 mass %, more preferably from 20 to 80 mass %, based on the total mass of the membrane components of the liposome. One kind of the hydrophobic iodine compound may be used as a membrane component, or two or more kinds of the hydrophobic iodine compounds may be used in combination.

As other membrane components constituting the liposome, any of lipid compounds ordinarily used for preparation of liposomes can be used. For example, such compounds are described in Biochim. Biophys. Acta, 150 (4), 44 (1982); Adv. in Lipid. Res., 16 (1) 1 (1978); "RESEARCH IN LIPOSOMES", P. Machy, L. Leserman, John Libbey EUROTEXT Co.; "Liposome" (Ed., Nojima, Sunamoto and Inoue, Nankodo) and the like. As the lipid compounds, phospholipids are preferred, and phosphatidylcholines (PC) are particularly preferred. Preferred examples of phosphatidylcholines include, but not limited thereto, egg PC, dimyristoyl-PC (DMPC), dipalmitoyl-PC (DPPC), distearoyl-PC (DSPC), dioleyl-PC (DOPC) and the like.

According to a preferred embodiment of the present invention, a phosphatidylcholines and a phosphatidylserine (PS) can be used in combination. Examples of the phosphatidylserines include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, further preferably 30:70 to 70:30.

Another preferred embodiment of the liposome of the present invention includes the liposome containing a phosphatidylcholine and a phosphatidylserine and further containing a phosphoric acid dialkyl ester as membrane components. The two alkyl groups constituting the dialkyl ester of phosphoric acid are preferably the same groups. Each group may contain 6 or more carbon atoms, preferably 10 or more carbon atoms, more preferably 12 or more carbon atoms. Preferred examples of the phosphoric acid dialkyl ester include, but not limited thereto, dilauryl phosphate, dimyristyl phosphate, dicetyl phosphate and the like. In this embodiment, preferred amount of the phosphoric acid dialkyl ester is from 1 to 50 mass %, preferably from 1 to 30 mass %, further preferably from 1 to 20 mass %, based on the total mass of phosphatidylcholine and phosphatidylserine.

In the liposome containing a phosphatidylcholine, a phosphatidylserine, a phosphoric acid dialkyl ester and a hydrophobic iodine compound as membrane components, preferred weight ratio of PC, PS, phosphoric acid dialkyl ester and hydrophobic iodine compound may be chosen from 5 to 40 mass %: from 5 to 40 mass %: from 1 to 10 mass %: from 15 to 80 mass %.

The components of the liposome of the present invention are not limited to the aforementioned four kinds of compounds, and other components may be added. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) etc., glucuronic acid derivatives described in Chem. Lett., 2145 (1989); Biochim. Biophys. Acta, 1148, 77 (1992) etc., polyethylene glycol derivatives described in Biochim. Biophys. Acta, 1029, 91 (1990); FEBS Lett., 268, 235 (1990) and the like. However, the components are not limited to these examples.

The liposome of the present invention can be prepared by any methods known in the field of the art. Examples of the preparation method are described in the references as general review of liposomes, which are mentioned above, as well as in Ann. Rev. Biophys. Bioeng., 9, 467 (1980), "Liopsomes" (Ed. by M. J. Ostro, MARCELL DEKKER, INC.) and the like. Specific examples include, but not limited thereto, the ultrasonication method, ethanol injection method, French press method, ether injection method, cholic acid method, calcium fusion method, freeze and thawing method, reverse phase evaporation method and the like. Size of the liposome of the present invention may be any of those obtainable by the aforementioned methods. Generally, a size in average may be 400 nm or less, preferably 200 nm or less. Structure of the liposome is not particularly limited, and may be unilamellar or multilamellar structure. It is also possible to formulate one or more kinds of appropriate drugs or other contrast media in the liposome.

When the liposomes of the present invention are used as a contrast medium, they can be preferably administered parenterally, more preferably administered intravenously. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium, the dose can be suitably determined so that an iodine content in the liposomes becomes similar to that of a conventional iodine-containing contrast medium.

Although it is not intended to be bound by any specific theory, it is known that, in vascular diseases such as arteriosclerosis or restenosis after PTCA, vascular smooth muscle cells constituting tunica media of blood vessel abnormally proliferate and migrate into endosporium at the same time to narrow blood flow passages. Although triggers that initiate the abnormal proliferation of normal vascular smooth muscle cells have not yet been clearly elucidated, it is known that migration of macrophages into endosporium and foaming are important factors. It is reported that vascular smooth muscle cells then cause phenotype conversion (from constricted to composite type).

When the liposomes of the present invention are used, the hydrophobic iodine compound can be selectively taken up into the vascular smooth muscle cells abnormally proliferated under influences of foam macrophages. As a result, radiography becomes possible with high contrast between a lesion and a non-pathological site. Therefore, the contrast medium of the present invention can be suitably used particularly for X-ray radiography of vascular diseases. For example, radiography of arteriosclerotic lesion or restenosis after PTCA can be performed. Method for imaging is not particularly limited. Imaging can be performed by, for example, a method utilizing X-ray irradiation, radionuclide imaging utilizing an radioactive iodine-labeled compound and the like. However, the method is not limited to these.

The method for producing a cell culture system provided by the present invention is characterized to comprise a step of culturing, in a single cell culture vessel, two or more kinds of cell species which are involved in formation of lesion of a mammalian disease. As the cell species, primary culture cells and established subculture cells are preferred, and mammalian primary culture cells are particularly preferred. Preferred mammals include, but not limited thereto, human, dog, cat, pig, miniature pig, rabbit, hamster, rat, mouse and the like. Type of the culture vessel is not particularly limited, and for example, culture flask, culture test tube, dish, microplate and the like can be suitably used.

The two or more kinds of different cell species cultured in a single culture vessel may be derived from homologous animals or heterogenous animals. They may preferably be derived from homologous animals. In the specification, the term "involved in formation of a lesion" should be construed in its broadest sense, including a condition where plural kinds of cells form a lesion under mutual control of proliferation and the like, and the term should not be construed in any limitative sense. As the different cell species, it is preferred to chose cell species different from cytobiological y or cytotaxonomical viewpoint. More preferably, two kinds of cell species may be chosen that coexist in a certain lesion and form the lesion under mutual control of proliferation. For example, macrophages and vascular smooth muscle cells, which coexist in an arteriosclerotic lesion, are preferably chosen as the two kinds of cell species.

In a preferred embodiment of the method for preparing a cell culture system of the present invention, the two kinds of cell species can be cultured in a single well under being partitioned off by means of a cell filter. According to another preferred embodiment of the present invention, the two kinds of cell species used are preferably cells that form an arteriosclerotic legion. Preferred cell species include macrophages, vascular smooth muscle cells, vascular endothelium cells, T cells, mast cells and the like. Among them, preferred cell species include macrophages, vascular smooth muscle cells and vascular endothelium cells, and particularly preferred cell species include a combination of macrophages and vascular smooth muscle cells. In the combination, the macrophages are preferably made into foam cells beforehand.

According to the present invention, a method is provided for evaluation of permeation ability of a drug into a lesion of a vascular disease, which comprises a step of measuring action of the drug on vascular smooth muscle cells which are proliferated by culturing foam macrophages and the vascular smooth muscle cells under being partitioned off by means of a cell filter. The term "action of drug" used in the specification should be construed in its broadest sense including therapeutic effect, diagnostic effect and the like. Types of the cell filter are not particularly limited so long as they have such a pore size that does not allow foam macrophages and vascular smooth muscle cells to pass through pores. For example, as a pore size that does not allow the cells to pass through pores, a filter having a pore size of 0.4 μm or less can be used. Depending on types of foam macrophages and cells to be used, a cell filter having an appropriate pore size can be easily chosen.

Although it is not intended to be bound by any specific theory, when foam macrophages and vascular smooth muscle cells are cultured under being partitioned off by means of a cell filter, a proliferation activating substance derived from the foam macrophages acts on the vascular smooth muscle cells to induce their proliferation, and thus abnormal proliferation of vascular smooth muscle cells in a vascular disease such as arteriosclerosis and restenosis after PTCA can be reproduced in vitro. Investigation of uptake of drugs into the proliferated vascular smooth muscle cells enables screening of a drug having a high effectiveness on vascular diseases such as arteriosclerosis and restenosis after PTCA.

EXAMPLES

The present invention will be explained more specifically with reference to the examples. However, the scope of the present invention is not limited to the following examples.

Example 1

Preparation of Culture System of Vascular Smooth Muscle Cells of which Proliferation is Activated by Foam Macrophages (1)

Vascular smooth muscle cells were isolated from mouse aorta endothelium ("Tissue Culture Method", 10th Edition, ed. by the Japanese Tissue Culture Association, published by Kodansha, 1998). The isolated vascular smooth muscle cells were suspended in 10% FBS Eagle's MEM (GIBCO, No. 11095-080) and inoculated in wells of a 12-well microplate (FALCON, No. 3503). The number of the cells in each well was adjusted to 10,000 cells. The cells were cultured for 3 days under conditions of 37° C. and 5% $CO_2$.

Figure 1:
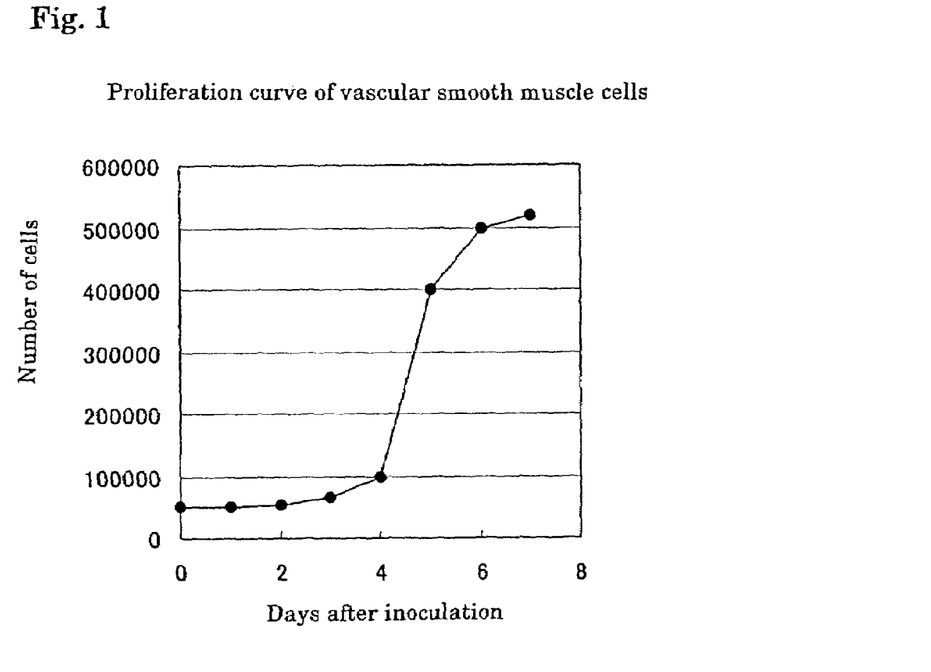
FIG. 1 shows results of induction of mouse vascular smooth muscle cell proliferation in the presence of foam mouse macrophages.
Figure 2:
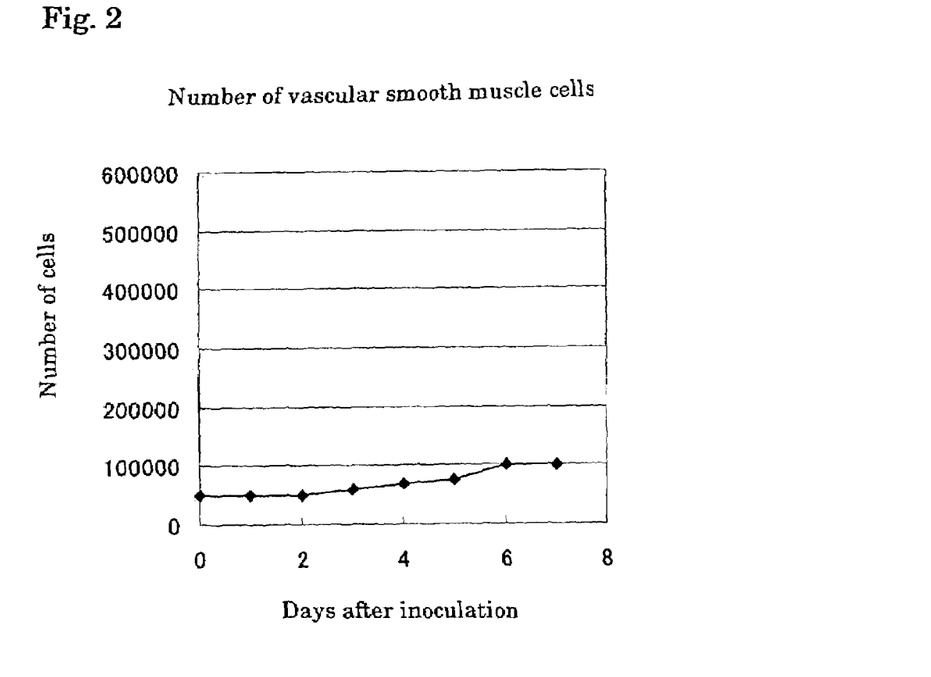
FIG. 2 shows a proliferation curve of mouse vascular smooth muscle cells obtained without addition of foam mouse macrophages.

Then, foam mouse peritoneal macrophages were prepared according to the method described in Biochimica Biophysica Acta, 1213, 127 (1994). 200,000 cells of the foam macrophages were separated and inoculated on an insert cell (FALCON, No. 3180) placed on each well of the microplate where the vascular smooth muscle cells were cultured on the bottom surface. The cells were cultured for 5 days under conditions of 37° C. and 5% $CO_2$. The cell numbers of the vascular smooth muscle cells in the above experiment are shown in FIG. 1. Although the vascular smooth muscle cells gently proliferated at an early stage after the start of the culture, they actively proliferated after the addition of the foam macrophages after 3 days and a subsequent induction period of about 1 day. A proliferation curve of vascular smooth muscle cells not added with the macrophages is shown in FIG. 2. Comparison of the results shown in FIGS. 1 and 2 clearly indicates activating effect of the foam macrophages on the proliferation.

Example 2

Verification of Expression of Scavenger Receptors on Vascular Smooth Muscle Cells It is known that vascular smooth muscle cells in an arteriosclerotic lesion express scavenger receptors on their surfaces to take up oxidized LDL (Biochem. Phamacol., 15:57 (4), 383–6 (1999); Exp. Mol. Pathol., 64 (3), 127–45, 1997). The vascular smooth muscle cells of the culture system of FIG. 1 were immunostained by using mouse scavenger receptor antibodies. As a result, although the expression was not observed on the vascular smooth muscle cells on the 3rd day from the inoculation, clear staining was observed on the 6th day from the inoculation. When the foam macrophages on the cell filter were also similarly immunostained, clear staining was also observed.

Example 3

Uptake of Oxidized LDL by Vascular Smooth Muscle Cells

In the culture system of FIG. 1, $^{125}$I-labeled oxidized LDL was added to the medium for the vascular smooth muscle cells on the 3rd day and 6th day from the inoculation. $^{125}$I taken up into the cells was counted 24 hours after each addition. The results are shown in Table 1. Clear difference in uptake amount was observed between the results on the 3rd day and 6th day. The above results indicate that the vascular smooth muscle cells cultured in the cell culture system of the present invention had properties similar to those of smooth muscle cells in a lesion of arteriosclerosis, restenosis or the like.

TABLE 1

| Day | Uptake of $^{125}$I-oxLDL |
| --- | --- |
| 3rd Day from inoculation | 0.52 ± 0.11 |
| 6th Day from inoculation | 2.2 ± 0.4 |
|  | ×10,000 cpm |

Example 4

Preparation of Culture System of Vascular Smooth Muscle Cells of which Proliferation is Activated by Foam Macrophages (2)

Figure 3:
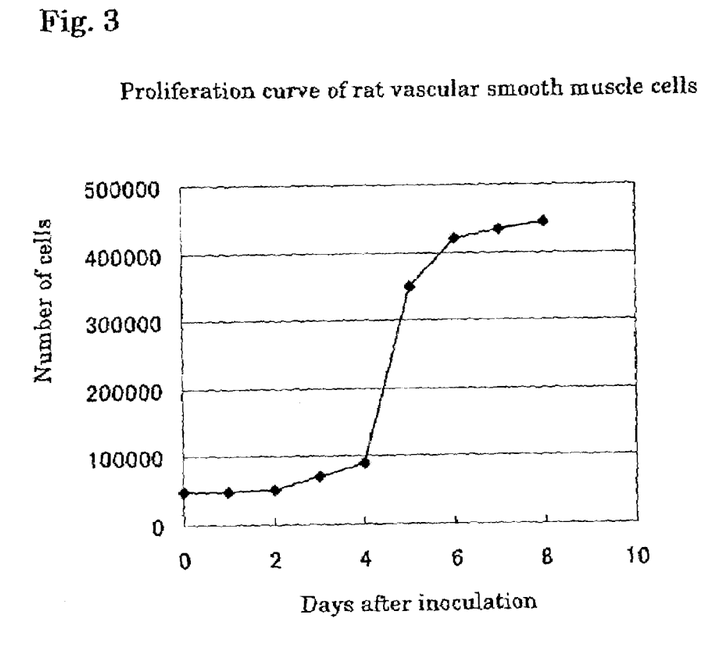
FIG. 3 shows results of induction of rat vascular smooth muscle cell proliferation in the presence of foam rat macrophages.
Figure 4:
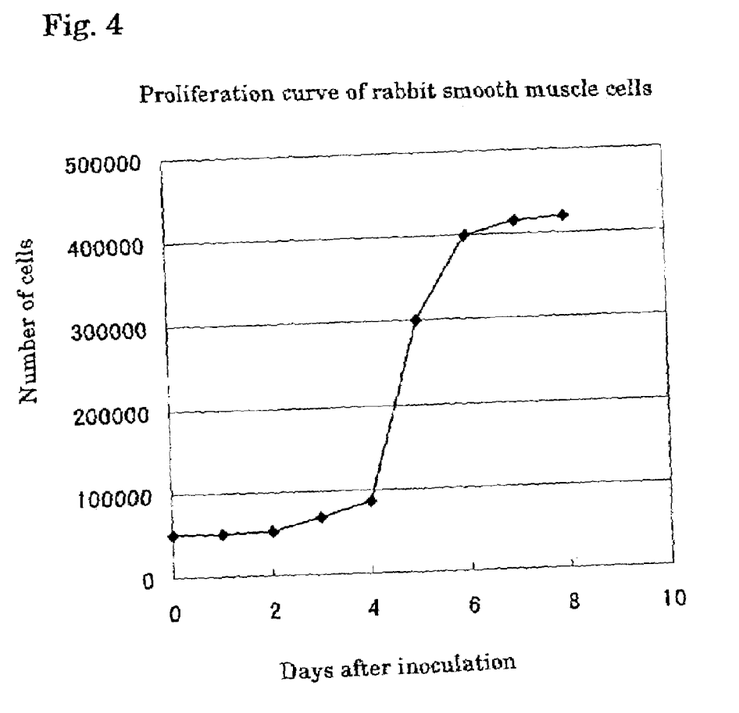
FIG. 4 shows results of induction of rabbit vascular smooth muscle cell proliferation in the presence of foam rabbit macrophages.

Culture systems comprising rat and rabbit macrophages and vascular smooth muscle cells were prepared in the same manner as in Example 1. The cell numbers of vascular smooth muscle cells are shown in FIGS. 3 and 4. In each of the experiments, a result similar to that of FIG. 1 for mouse was obtained.

The vascular smooth muscle cells cultured in the culture system in FIG. 1 had properties of healthy blood vessel until the 3rd day from the inoculation and properties of smooth muscle cells in an arteriosclerotic lesion on and after the 7th day from the inoculation. Accordingly, a screening of a drug selective to the lesion can be performed by comparing actions of the drug on each of the above cells. In particular, the system can be utilized for searching of a drug delivery system selective to a lesion, searching of a drug that is selectively toxic for cells in a lesion, searching of a drug that selectively terminates cell cycle of cells in a lesion and the like. Specific examples will be given below. However, the present invention is not limited to these examples.

Example 5

Preparation of Liposomes

Egg PC (Funakoshi, No. 1201-41-0214), egg PS (Funakoshi, No.1201-42-0226), dicetyl phosphate (DCP, Funakoshi, No.1354-14-8165) and Hydrophobic iodine compound (3) synthesized by the method described in J. Med. Chem., 25 (12), 1500 (1982), in the ratios described blow, were dissolved in methylene chloride contained in an eggplant-shaped flask to form a uniform solution, and then the solvent was evaporated under reduced pressure to form a thin membrane on the bottom of the flask. The thin membrane was dried in vacuo, then added with 1.5 ml of 0.9% physiological saline (Hikari Pharmaceutical, No. 512) and ultrasonicated (probe type oscillator, Branson, No.3542, 0.1 mW) for 5 minute with ice cooling to obtain a uniform liposome dispersion. Size of the particles contained in the resulting dispersion was measured by using WBC analyzer (Nihon Kohden, A-1042). The particle size was 40 to 65 nm.

| Liposome | PC | PS | DCP | Compound (3) |
| --- | --- | --- | --- | --- |
| Preparation 1 | 50 nmol | 50 nmol | 10 nmol | 40 nmol |
| Preparation 2 | 50 nmol | 50 nmol | 10 nmol | 75 nmol |
| Preparation 3 | 50 nmol | 50 nmol | 10 nmol | 150 nmol |

Example 6

Selective Uptake of Liposome Preparations by Vascular Smooth Muscle Cells (1)

The three types of liposomes prepared in Example 5 were added to the smooth muscle cell culture system of FIG. 1 or 2 in Example 1 according to the following conditions (1), (2) and (3), and then the culture was continued.

(1) A liposome preparation was added after 3 days to the culture system of FIG. 2 not added with the foam macrophages, and culture was continued for 1 day.

(2) A liposome preparation was added after 5 days to the culture system of FIG. 1 added with the foam macrophages, and culture was continued for 1 day.

(3) A liposome preparation was added after 7 days to the culture system of FIG. 1 added with the foam macrophages, and culture was continued for 1 day.

Figure 5:
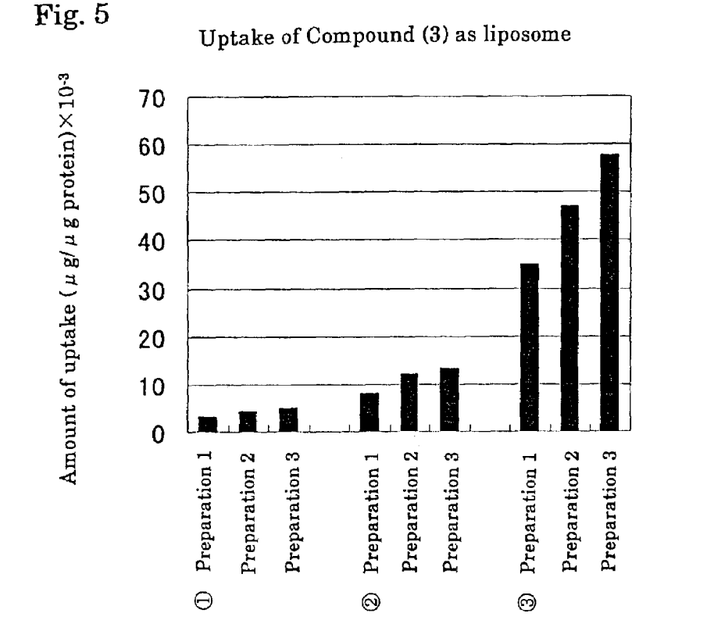
FIG. 5 shows uptake of liposomes by mouse vascular smooth muscle cells. In the figure, (1) shows results obtained by adding a liposome preparation after 3 days to the culture system of FIG. 2 not added with foam macrophages, and then continuing the culture for 1 day, (2) shows results obtained by adding a liposome preparation after 5 days to the culture system of FIG. 1 which was added with foam macrophages, and then continuing culture for 1 day, and (3) shows results obtained by adding a liposome preparation after 7 days to the culture system of FIG. 1 which was added with foam macrophages, and then continuing culture for 1 day.

After addition of liposomes and post-culture according to each of the conditions (1) to (3) were completed, the supernatant was removed, and the residue was washed three times with Hank's buffer (Nissui Pharmaceutical, Code 05906, pH 7.2), then added with 1.5% SDS solution (Wako Pure Chemical Industries, 199-07141) and incubated at 37° C. for 30 minutes to lyse the cells. Then, amount of Compound (3) taken up into the cells was measured by HPLC. The results are shown in FIG. 5. Clear differences in the amounts of the iodine compound taken up into the vascular smooth muscle cells from the liposomes of the present invention were observed before and after the proliferation was initiated under influence of the foam macrophages.

Example 7

Comparative Example

Figure 6:
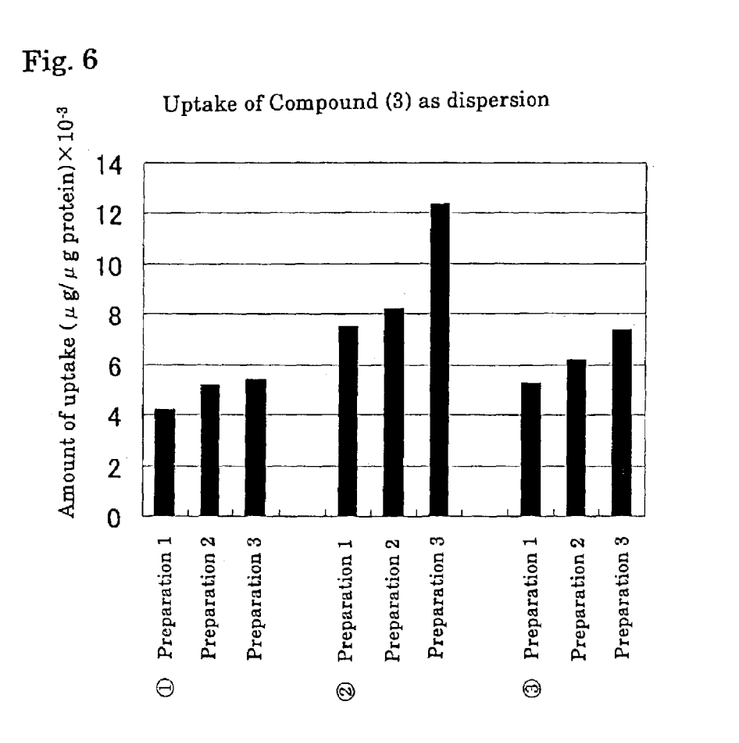
FIG. 6 shows the results obtained by using an oil-particle dispersion instead of the liposomes of the present invention.

An oil particle suspension of Compound (3) was prepared according to the method described in Pharm. Res., 16, (3) 420 (1999). The suspension was added to the cell culture system under the same conditions as those used in Example 6 (conditions (1), (2) and (3)) with the same amount of Compound (3), and amounts of Compound (3) taken up into the vascular smooth muscle cells were measured by HPLC. The results are shown in FIG. 6. From comparison of the results shown in FIGS. 5 and 6, it is clearly understood that, by using the liposomes of the present invention, the iodine-containing contrast medium can be more efficiently and more selectively accumulated than the known oil particle suspension in the vascular smooth muscle cells abnormally proliferating under influence of foam macrophages.

Example 8

Selective Uptake of Liposome Preparations by Vascular Smooth Muscle Cells (2)

Figure 7:
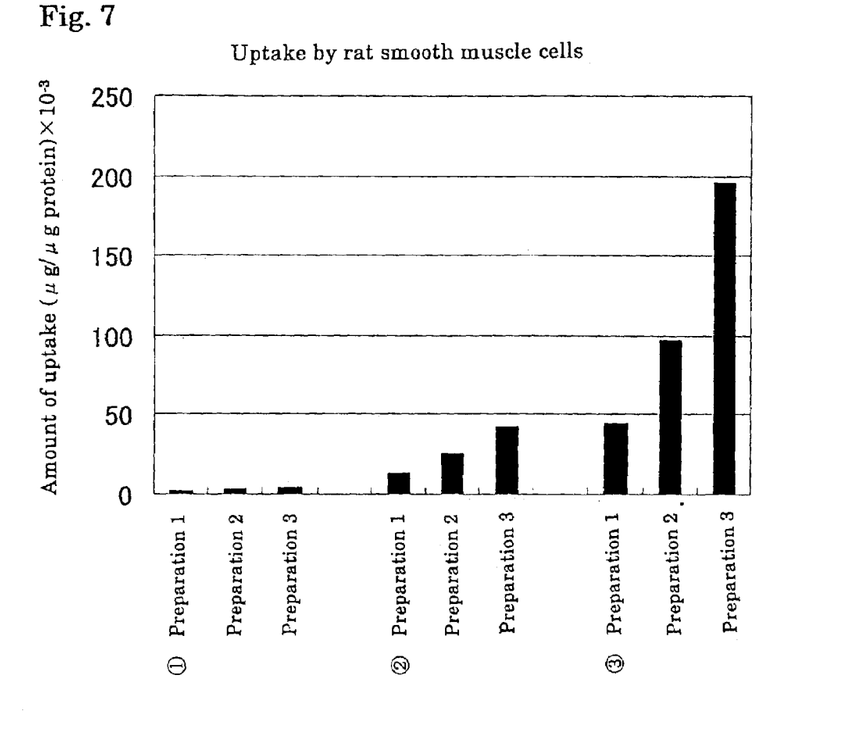
FIG. 7 shows uptake of liposomes by rat vascular smooth muscle cells cultured under the culture conditions mentioned in FIG. 3. In the figure, (1), (2) and (3) have the same meanings as those mentioned in FIG. 5.
Figure 8:
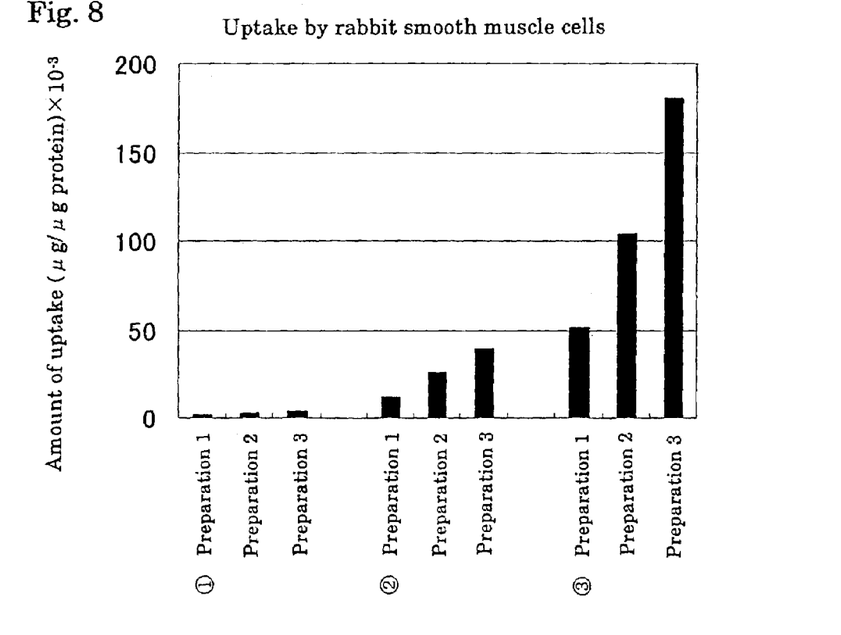
FIG. 8 shows uptake of liposomes by rabbit vascular smooth muscle cells cultured under the culture conditions mentioned in FIG. 4. In the figure, (1), (2) and (3) have the same meanings as those mentioned in FIG. 5.

The three types of liposomes prepared in Example 5 were added to the smooth muscle cell culture systems of rat (FIG. 3) and rabbit (FIG. 4) prepared in Example 4 according to the aforementioned conditions (1), (2) and (3), and the culture was continued. Amounts of Compound (3) taken up into the cells were measured by HPLC. The results are shown FIGS. 7 and 8. Each system gave results similar to those shown in FIG. 5 for mouse cells.

Example 9

Figure 9:
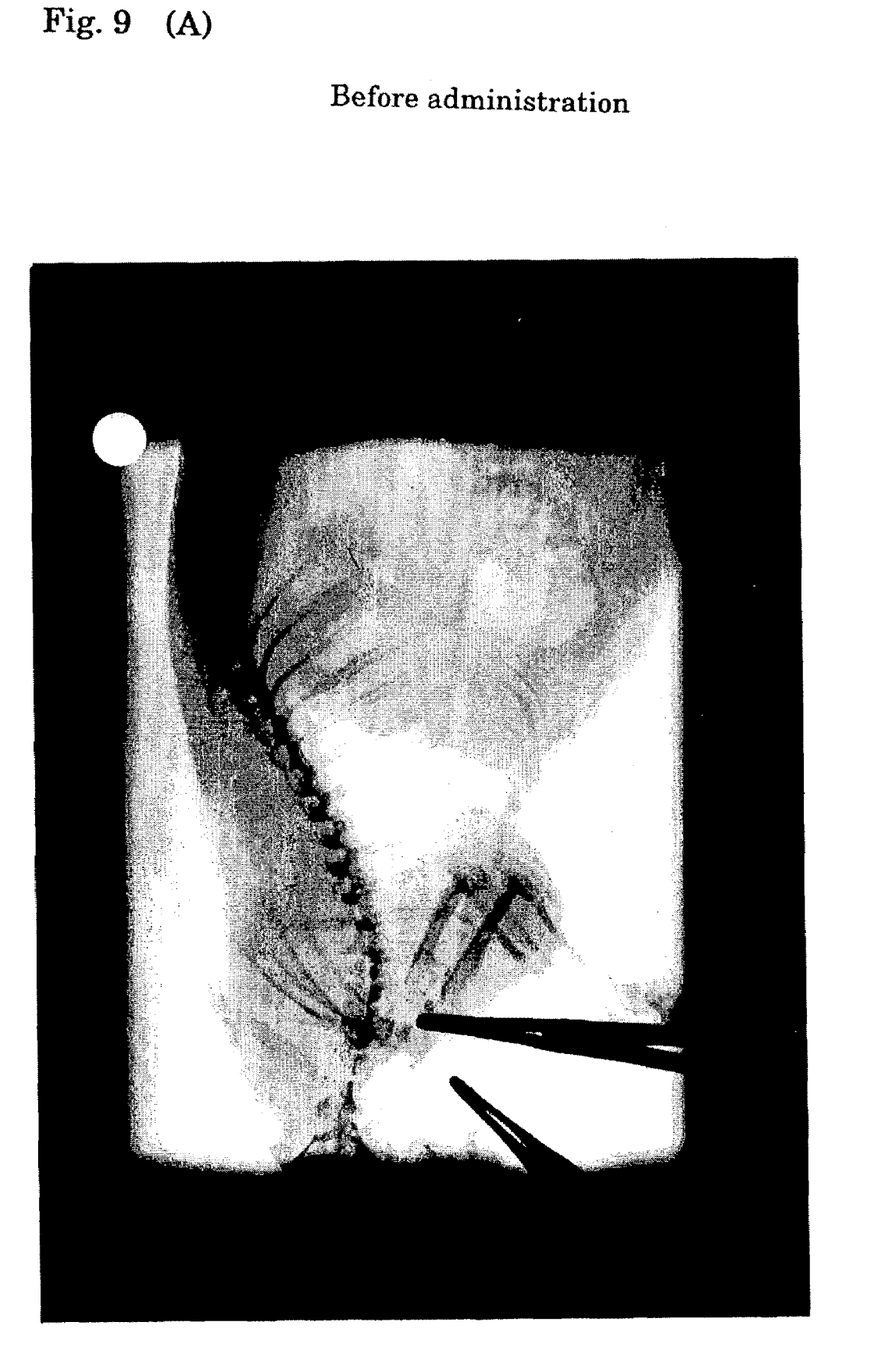
FIG. 9 depicts photographs showing the results of X-ray radiography of arteriosclerotic lesions by using the liposomes of the present invention. In the figure, "before administration" indicates the result obtained before administration of liposomes, and "after administration" indicates the result obtained immediately after administration of liposomes.
Figure 10:
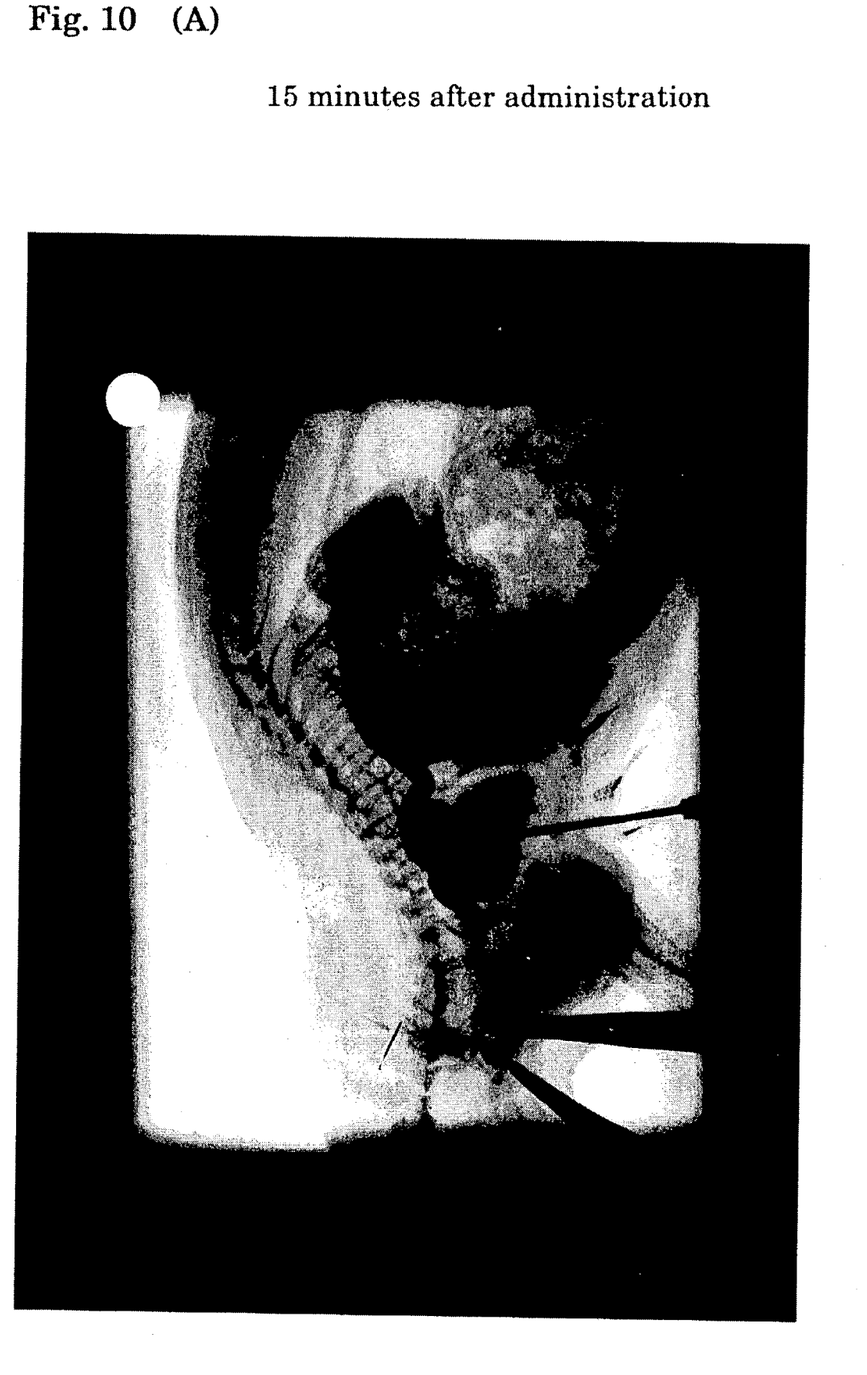
FIG. 10 depicts photographs showing the results of X-ray radiography of arteriosclerotic lesions using the liposomes of the present invention. In the figure, "15 minutes after administration" indicates the result obtained 15 minutes after administration of liposomes, and "30 minutes after administration" indicates the result obtained 30 minutes after administration of liposomes.

Arteriosclerotic lesions were formed in a rat aorta according to the method described in Invest. Radiol. 18, 275 (1983). Liposome preparation 3 prepared in Example 2 was carefully administered to the rat in which arteriosclerotic lesions were formed in an amount of 200 mg/kg as an MTD amount converted to be an amount of Compound (3). Thirty minutes after the administration, clear X-ray radiographic photographs of the arteriosclerotic lesions was obtained. The results are shown in FIGS. 9 and 10.

INDUSTRIAL APPLICABILITY

The liposomes of the present invention can achieve accumulation of iodine compounds in vascular smooth muscle cells abnormally proliferating under influence of foam macrophages, and are useful as an X-ray contrast medium for selective radiography of a lesion of a vascular disease caused by abnormal proliferation of vascular smooth muscle cells. Further, the culture systems provided by the method for preparing a culture system of the present invention can be utilized, as cell culture systems in which a state of lesion of arteriosclerosis, restenosis or the like is reproduced, for in vitro screening of drugs and the like.

What is claimed is:

1. A liposome containing a hydrophobic iodine compound as a membrane component, wherein the hydrophobic iodine compound is a 1, 3, 5,-triiodobenzene derivative having at least one substituent which contains 18 or more carbon atoms and which is a residue of a cholesterol derivative.

2. The liposome according to claim 1, which contains a lipid selected from the group consisting of phosphatidylcholines and phosphatidylserines as a membrane component.

3. The liposome according to claim 1, which contains a phosphoric acid dialkyl ester as being a diester of an alkyl containing 6 or more carbon atoms as a membrane component.

4. An X-ray contrast medium, which comprises a liposome according to claim 1.

5. The X-ray contrast medium according to claim 4, which is used for radiography of a vascular disease.

6. The X-ray contrast medium according to claim 4, which is used for radiography of vascular smooth muscle cells abnormally proliferated under an influence of foam macrophages.

* * * * *